(12) United States Patent
Straub et al.

(10) Patent No.: US 6,482,076 B1
(45) Date of Patent: Nov. 19, 2002

(54) METHOD FOR PRODUCING A SURFACE STRUCTURE, IN PARTICULAR ON A SURGICAL IMPLANT

(75) Inventors: Werner Straub, Oberstammheim; Christoph Sprecher, Davos Dorf; John Antony Peters, Winterthur; Markus Windler, Hofstetten, all of (CH)

(73) Assignee: Sulzer Innotec AG, Winterthur (CH)

( * ) Notice: Subject to any disclaimer, the term of this patent is extended or adjusted under 35 U.S.C. 154(b) by 0 days.

(21) Appl. No.: 09/594,110

(22) Filed: Jun. 13, 2000

(30) Foreign Application Priority Data

Jul. 19, 1999 (EP) .............................. 99810651

(51) Int. Cl.[7] .............................. B24B 1/00; B24C 1/00
(52) U.S. Cl. .............................. 451/38; 451/36
(58) Field of Search .............................. 451/28, 36, 37, 451/38, 39, 40, 60, 75, 91, 99, 102

(56) References Cited

U.S. PATENT DOCUMENTS 5,681,616 A 10/1997 Gupta

FOREIGN PATENT DOCUMENTS

EP    0 417 034 A1    3/1991

OTHER PUBLICATIONS

H. Hocheng, et. al.: "Feasibility Study of Abrasive–Waterjet Milling of Fiber–Reinforced Plastics" *Journal of Manufacturing Science and Engineering*; 5/97, vol. 119, pp. (133–142).

A. Momber, "Aktuelle Probleme Der Abrasiv–Wasserstrahl–Bearbeitung" Werkstattstechnik, De Springer Verlag. Berlin, vol. 81, No. 7, pp. (437–441).

M. Knaupp, "Prozesskontrolle Beim Hochdruckwasser–und Wasserabrasivstrahlshneiden" VDI Z, De VDI Verlag GmbH. Dusseldorf, vol. 135 pp. (6–11).

CH. Wulf, "Qualitaetsbestimmende Einflussgroessen beim Wasserstrahlschneiden" Industrie Anzeiger, De Konradin Verlag, Leinfelden, vol. 105, No. 70, Sep. 2, 1983, pp. (101–102).

*Primary Examiner*—Derris H. Banks
(74) *Attorney, Agent, or Firm*—Townsend and Townsend and Crew LLP

(57) ABSTRACT

In the method for producing a surface structure, material is ablated by means of a liquid jet (1). The jet (1) is emitted from a nozzle (10) under high pressure (p). In this an ablation location (3) is controlledly moved on a surface (20a) of a substrate (20) to be structured with the production of a predetermined macro-topography (2') or a largely planar surface, namely through moving the nozzle and/or the substrate. The substrate is in particular part of a surgical implant. The liquid of the high pressure jet (1) is emitted at a predetermined diameter d of the nozzle with a sufficiently high pressure p so that through the material ablation a linear track (2) with quasi-fractal micro-topography (4) is produced. In this the track width D is at least twice as large as d. Values for p and d are provided in the following range: 100 bar<p<3000 bar and 0.1 mm<d<10 mm; or p>3000 bar and d>0.03 mm.

11 Claims, 4 Drawing Sheets

METHOD FOR PRODUCING A SURFACE STRUCTURE, IN PARTICULAR ON A SURGICAL IMPLANT

Figure 1:
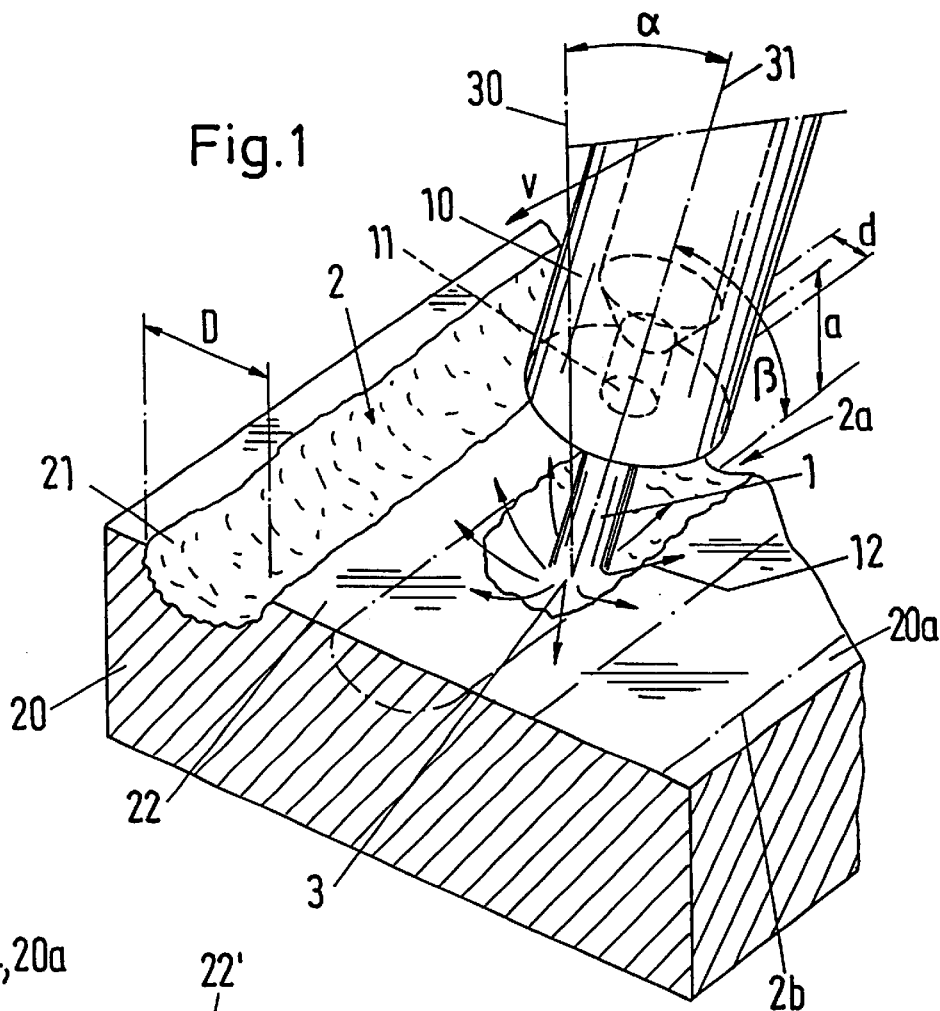

The invention relates to a method for producing a surface structure, in particular on a surgical implant, in accordance with the preamble of claim 1, to a plant for carrying out the method and to uses of the method.

An implant which has anchoring surfaces for bone tissue is known from EP-A 0 417 034 (=P.6300). In this the anchoring surface is produced by means of a method in which three-dimensional geometric forms are produced using a high pressure liquid jet. In order to be able to achieve a suitable depth action with the liquid jet, abrasive particles are admixed to the liquid. These particles, traces of which remain in the depressions produced, must be compatible with the human body. In this known method it is assumed that with a high pressure jet which is linearly guided over a substrate, a groove-like ablation track arises in the substrate, the width of which is largely of the same size as the jet diameter or the diameter of the nozzle used.

The object of the invention is to create a method for producing a surface structure through material ablation by means of a liquid jet in which an ablation track arises which is particularly advantageous with respect to physiological processes as a result of the micro-structure or micro-topography which is produced. Such physiological processes are understood to include for example the growing on and in of bone tissue in a hip joint prosthesis or an electrophysiological influence on a tissue to be stimulated for example through a heart pacemaker electrode. This object is satisfied by the method which is characterized in claim 1.

In the method for producing a surface structure, material is ablated by means of a liquid jet. The jet is emitted from a nozzle under high pressure. In this an ablation location is controlledly moved on a surface of a substrate to be structured with the production of a predetermined macro-topography or a largely planar surface, namely through moving the nozzle and/or the substrate. The substrate is in particular part of a surgical implant. The liquid of the high pressure jet is emitted at a predetermined diameter d of the nozzle with a sufficiently high pressure p so that through the material ablation a linear track with quasi-fractal micro-topography is produced. In this the track width D is at least twice as large as d. Values for p and d are provided in the following range:

100 bar<p<3000 bar and 0.1 mm<d<10 mm;
or p>3000 bar and d>0.03 mm.

The method in accordance with the invention can also be advantageous in surface treatments in which non medical objects are treated:
a) the production of structures on homogeneous, quasi-isotropic materials in order for example to achieve a corrugation or an orange skin effect;
b) the structuring of inhomogeneous materials, with different behavior being used relative to solubility or erosion rates.

Subordinate claims 2 to 6 relate to advantageous embodiments of the method in accordance with the invention. The subject of claims 7 and 8 is a plant for carrying out the method. Claims 9 to 11 relate to uses of the method.

Figure 2:
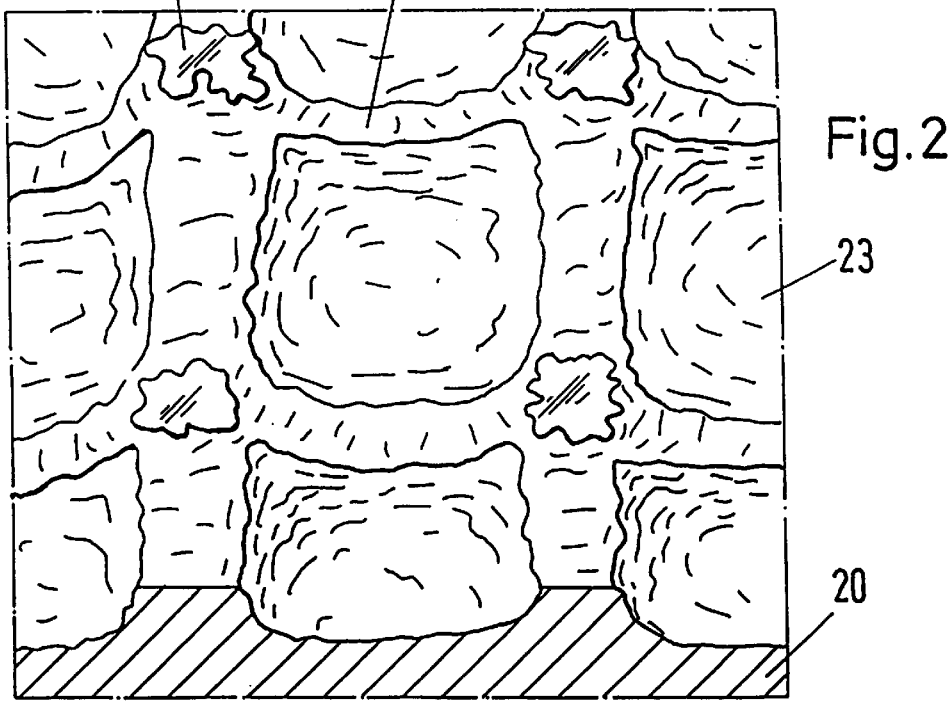
Figure 3:
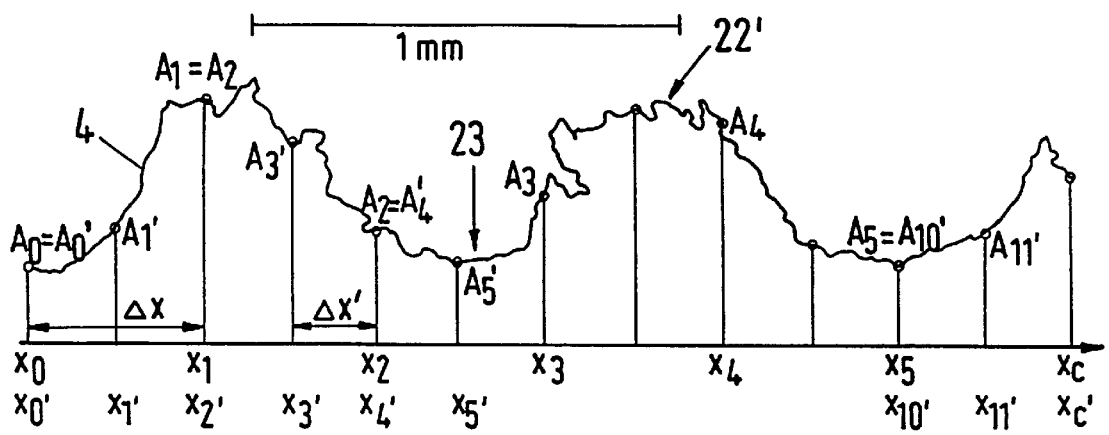
Figure 4:
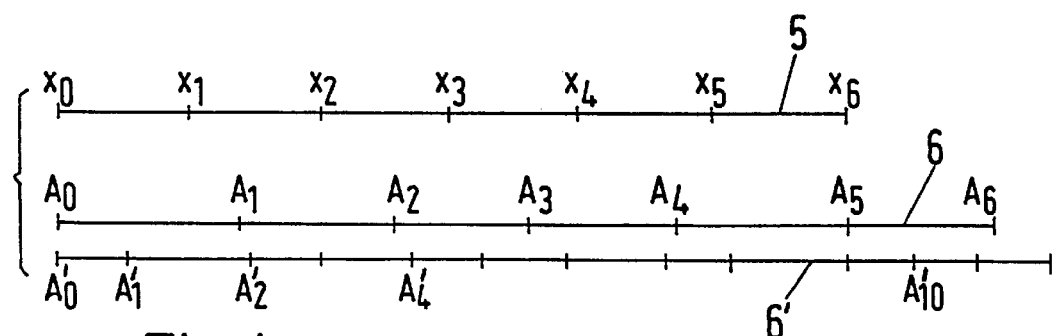
Figure 5:
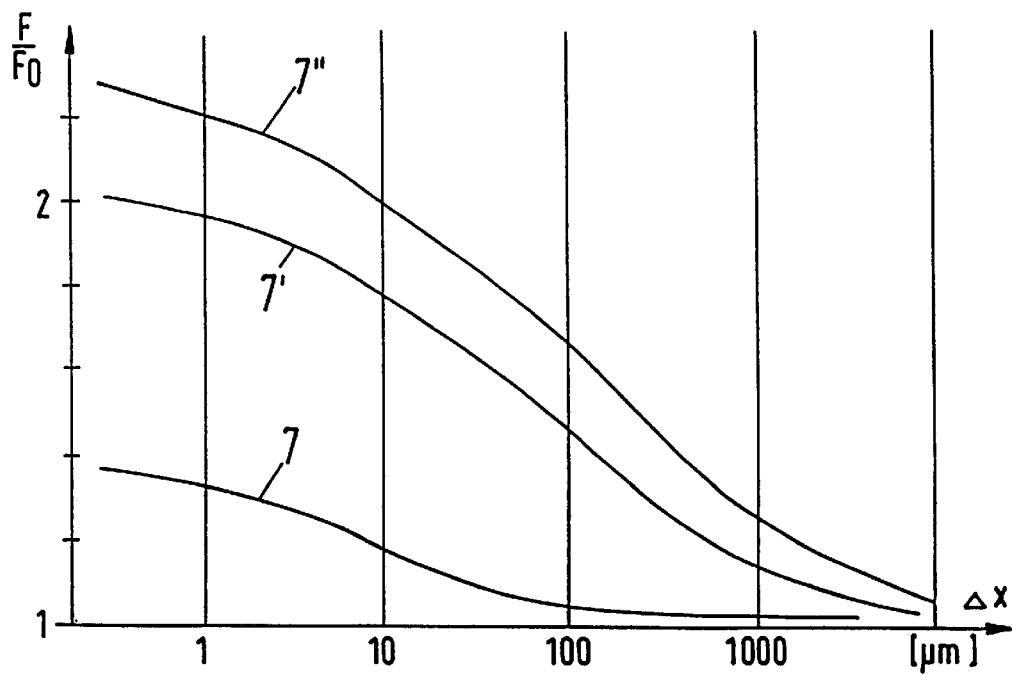
Figure 6:
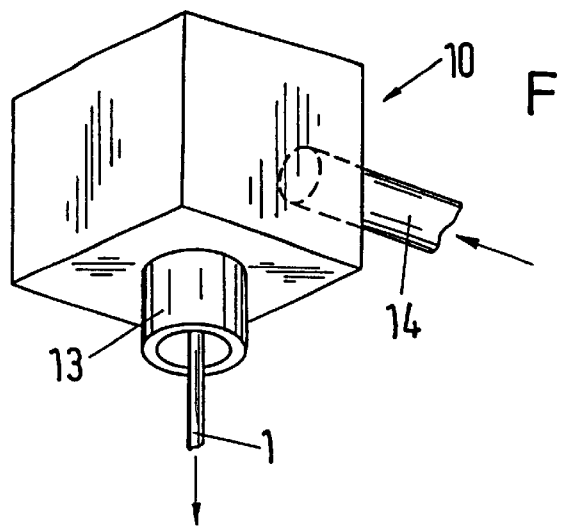
Figure 7:
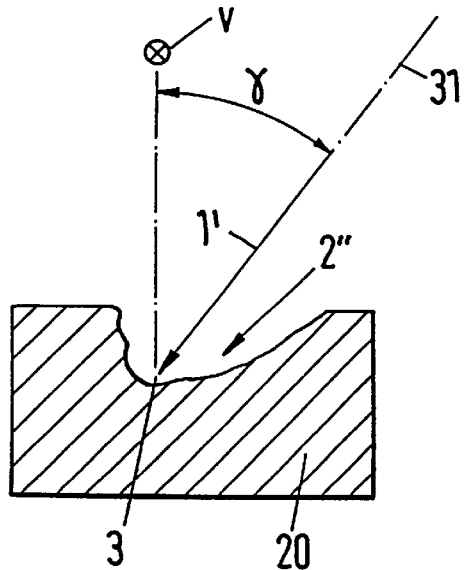
Figure 8:
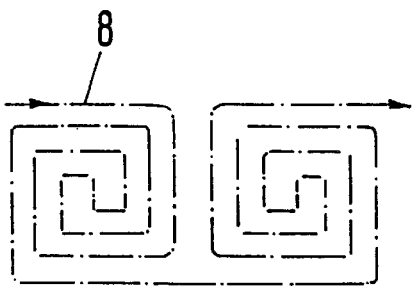
Figure 9:
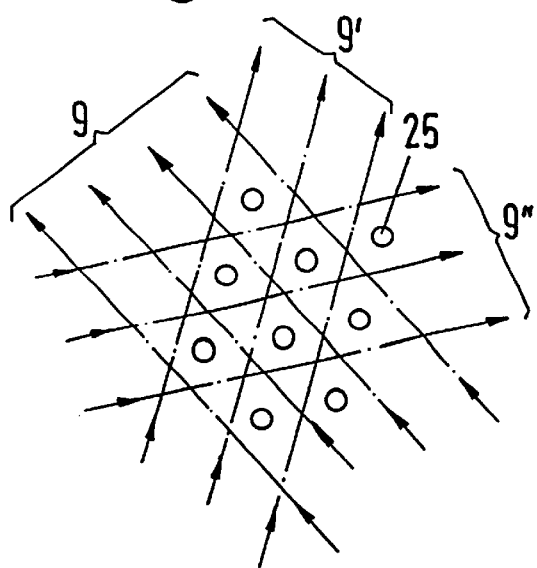
Figure 10:
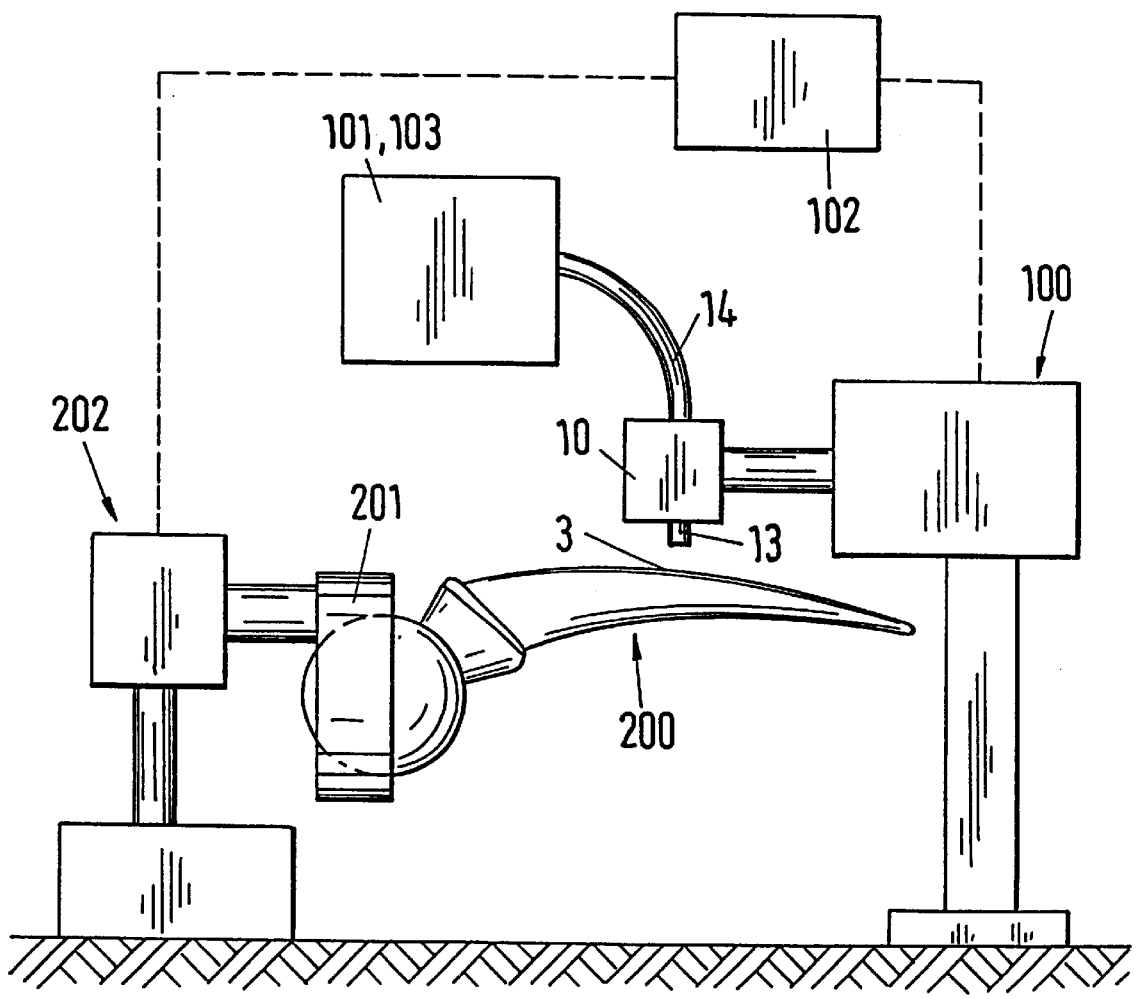

The invention will be explained in the following with reference to the drawings; in which represents:

FIG. 1 a material ablation in the form of rectilinear ablation tracks which is carried out with the method in accordance with the invention by means of a high pressure liquid jet, FIG. 2 a result of the method in accordance with the invention, FIG. 3 a profile of a surface which is processed in accordance with the invention, FIG. 4 partial results of a fractal analysis of the profile of FIG. 3, FIG. 5 diagrams on fractal analyses, FIG. 6 a nozzle head with a collimator tube, FIG. 7 a profile of an asymmetrical ablation track, FIG. 8 a centerline of a meander-like ablation track, FIG. 9 center lines of ablation tracks which are produced with three groups of mutually crossing, rectilinear tracks, and FIG. 10 a plant for carrying out the method in accordance with the invention.

In a material ablation by means of a high pressure liquid jet 1 such as is shown in FIG. 1, rectilinear, groove-like ablation tracks 2 are produced on a substrate 20. The jet 1 emerges from an outlet opening 11 of a nozzle 10, which is moved with a velocity v in the direction of the track 2a which is to be produced. It is incident on the surface 20a of the substrate 20 in an influence zone 3 (ablation location). Outlines of ablation tracks which will then arise on continuation of the ablation process are indicated by chain-dotted lines 2b.

A straight line 31, which as center line indicates the direction of the jet 1, is inclined by an angle a with respect to a normal 30 to the surface 20a. The angle $\alpha$ advantageously amounts to about 30° in the processing of different metallic alloys; the material ablation is particularly effective for this angle. The outlet opening 11 of the nozzle 10 has a diameter d; it is located at a distance a from the influence zone 3. The diameter d, namely the nozzle diameter, is substantially also the diameter of the emerging jet 1.

Water, which should in particular be treated in the production of surface structures on surgical implants, is advantageously used as the liquid for the high pressure jet, with it being possible for a treatment to comprise filtering, demineralizing and the addition of additional substances. It is however also possible to use a liquid which acts in an etching manner on the substrate. Solid particles which develop an abrasive action in the influence zone 3 during impact can also be suspended in the liquid. In surgical implants it can be advantageous to work without solid particles of this kind so that no contamination of the surface to be processed arises through residues of the solid particles. Bio-compatible solid particles which are inert, bio-active or degradable can however also be used. A bio-active substance is for example pentacalcium phosphate (hydroxyapatite) or another calciumphosphorus compound through which a bone growth is furthered.

The jet 1 strikes particles out of the surface 20a in the influence zone 3, which are flushed off laterally. The laterally flowing away liquid 12 removes further material from the substrate 20 with the co-operation of the liberated particles. A groove 2 of width D, which is at least twice as large as the nozzle diameter d, thus arises. The thus exposed surface 21 of the groove 2 has a rugged surface microtopography, which can be designated as "quasi-fractal" (cf. the following explanations on fractal analyses in connection with FIGS. 3 to 5). If the lines 30 and 31 lie in the same plane as the vector of the velocity v, then a shape of the groove 2 results, the cross-section of which is symmetrical.

Tests yielded the following results:
a) At a nozzle diameter d=0.13 mm, a jet pressure p of 3000 bar and an advance speed v of 250 mm/min a well developed track with a width D which fluctuates between a minimum value of $D_{min}$=0.30 mm and $D_{max}$=0.60 mm arose. The ratio of $D_{min}/d$ is thus 2.31.

b) At d=0.18 mm, p=1500 bar and v=1500 mm/min the result was $D_{min}$=0.50 mm and $D_{max}$=0.70 mm; as a result $D_{min}/d$=2.78.

c) At d=0.40 mm, p=3500 bar and v=100 mm/min the result was $D_{min}$=0.90 mm and $D_{max}$=1.10 mm; as a result $D_{min}/d$=2.25.

The high pressure jet 1 is as a rule sprayed continuously onto the substrate 20. It is however also possible to use a pulsed jet 1.

In the method illustrated in FIG. 1 a macro-topography arises which is formed by parallel, rectilinear ablation tracks 2. A ridge 22 is left standing between adjacent tracks 2. The individual tracks 2 can however also be arranged very closely next to one another so that practically no ridges 22 can be recognized any longer: A largely planar surface with a quasi-fractal micro-topography arises.

To a first group of rectilinear tracks 2, such as can be produced with a surface processing in accordance with FIG. 1, a second group can be applied which is arranged crosswise to the first one. The result 2' of a macro-topography which is produced in this way is illustrated in FIG. 2 (drawn from a REM image). The relief structure 2' produced is chequered. The individual areas are hollows 23 which are bounded one from the other by combs 22'. Islands with residues of the original surface 20a of the substrate 20 are visible in the corner points of these areas. The processed material is a titanium alloy (Ti-6Al-4V: titanium with 6% aluminum by weight and 4% vanadium by weight). The distance between the corner points amounts to 1 mm. A nozzle was used, the diameter of which amounted to 0.18 mm. Water at a pressure of 3500 bar was used as the liquid.

A grid structure, such as is illustrated in FIG. 2, can also be produced in a more rational manner with a multiple nozzle in which a group of parallel tracks 2 can be simultaneously produced with a number of nozzle openings which are arranged in a row of equidistant points.

FIG. 3 shows the profile of a cross-section through the relief structure 2' shown in FIG. 2. The profile is illustrated as a curve 4 over an x axis. The x axis is subdivided uniformly into intervals $\Delta x$ or $\Delta x'$ ($=\frac{1}{2}\Delta x$) respectively by points $x_0$, $x_1$, ... or $x_0'$, $X_1'$.... These subdivisions correspond to points $A_0$, $A_1$, ... or $A_0'$, $A_1'$... respectively. The lengths of the paths $A_0$, $A_1$, ... or $A_0'$, $A_1'$... respectively are determined and compared. A graphical comparison is given in FIG. 4. The total path 5 represents the length on the x axis; the total paths 6 and 6' represent the lengths of the paths $A_0$, $A_1$, ... or $A_0'$, $A_1'$... respectively. Obviously the finer the subdivision $\Delta x$ of the x axis is, the greater these lengths are. This length as a function of $\Delta x$ provides a measure for the fractality of the profile 4. If this function continuously increases with decreasing $\Delta x$, and indeed up to a minimum $\Delta x$ which can not be dropped below for reasons of measuring technique, then the designation "quasi-fractal" will be used here for the micro-topography of the measured profile. In a common fractal analysis one proceeds somewhat differently: The path sections between neighboring points $A_1$ are given as constant values (so that the intervals $\Delta x$ are variable).

The diagram of FIG. 5 shows results of a corresponding fractal analysis for three samples of commercially pure titanium cpTi. In this analysis the enlargement of a surface F, the surface elements of which are triangles, is determined instead of an increase in lengths. The results for F are entered in the diagram—in relation to the basic surface $F_0$.

The three curves 7, 7' and 7" were won on the basis of rolled samples of Ti which were roughened by means of a group of parallel tracks 2 (displacement of adjacent tracks: b), with the method parameters being chosen as follows: d=0.25 mm, a=15 mm, b=0.20 mm, p=3500 bar, v=1.25 m/min (curve 7"), v=2.00 m/min (curve 7') and v=5.00 m/min (curve 7).

The distance a between the outlet opening 11 of the nozzle 10 and the influence zone 3 can amount to between about 0.1–20 mm. The angle β between the liquid jet 1 (β=90°−α) and the ablation track 2 produced can amounts to 90° (i.e. α=0°), but is however preferably chosen to be less than 90° in order thereby to obtain a more effective material ablation. Since the nozzle head in usual devices is designed to be relatively voluminous, there are difficulties in the setting of the jet direction if the jet is to be incident at an acute angle onto the substrate 20. Attachment of a collimator tube 13 ahead of the outlet opening 11—see FIG. 6—enables angles to be set which deviate from the normal 30 by at least 30°. The collimator tube 13 screens the jet 1 off from the surroundings so that the distance a between the outlet opening 11 and the influence zone 3 can be greater than the named distance of 20 mm without a substantial impairment in the quality of the jet 1. In FIG. 6 a connector tube 14 is shown in addition, through which the high pressure liquid is fed into the nozzle 10.

If the jet 1 is directed to the substrate 20 in accordance with the arrow 1' in FIG. 7, so that the jet center line 31 does not lie in the plane determined by the normal 30 and the velocity v, then a track 2" with an asymmetrical cross-section arises. In the example shown the straight lines 31 and 30 enclose—seen in the direction of the velocity v—an angle γ in the influence zone 3.

The ablation track 2 need not be rectilinear as in the examples of the FIGS. 1 and 2. It can for example also—as illustrated in FIG. 8—be led along a meander-like curve 8. If the curve 8 is the center line of a sufficiently wide ablation track 2, so that no ridges are formed between adjacent curve sections, then a relatively broad ablation strip results through the meander in a single transit.

As a rule each ablation track can be deepened by a single or multiple repetition of the ablation transit. If however in a first transit the surface to be processed remains largely intact, further transits do not lead as a rule to the development of a useful ablation track. It can however be the case that individual crater-like depressions arise in a first transit along the ablation curve. These depressions can then enlarge in further transits and finally lead to a completely excavated groove.

Whereas a macro-topography is illustrated in FIG. 2 which is produced with two groups of crossing, rectilinear tracks, FIG. 9 shows a corresponding pattern of ablation tracks in which the surface structuring is formed with three groups 9, 9', 9". Only the center lines to the ablation tracks are illustrated. The locations at which island-like elevations—corresponding to the islands 24 in FIG. 2—can remain standing are marked with small circles 25.

The method in accordance with the invention can also be combined with other methods: in a first or second step a further method for a surface processing, for example a sand blasting or a coating method, can be used. In the case of a sand blasting method the latter is preferably applied in the first step in order to be able to eliminate contaminations which are possibly caused by sand particles in a second step, which is carried out with a particle-free liquid.

A particularly advantageous use of the method in accordance with the invention is the surface structuring in a joint prosthesis which is provided for a cementless implantation. In this prosthesis the shaft surface must be suitably structured in order that a bone growth is furthered. The described quasi-fractal micro-topography is particularly suitable in this situation. A macro-topography such as is illustrated in FIG. 2 additionally enables a good anchoring during the initial phase, during which a connection between the bone and the prosthesis is still very weakly developed. A corresponding use is also advantageous in a dental implantation in which the implant in a jaw must gain a stable hold through a bone growth. The method in accordance with the invention can also be used in joint prostheses which are implanted using a cement in order to roughen zones of the surface to which the cement must adhere.

A further advantageous use of the method in accordance with the invention relates to electro-physiological electrodes, for example in heart pacemakers or defibrillators. In electrodes of this kind poles must be structured on their surfaces in order to—thanks to a greater specific surface—obtain a more effective energy transfer from the pole to a tissue which is to be influenced physiologically. As voltage measurements have shown, the quasi-fractal micro-topography is also particularly suitable here.

A plant for carrying out the method in accordance with the invention is illustrated in FIG. 10. It comprises the following: means for producing a relative velocity between the body 200 to be treated (here a hip joint prosthesis) and the ablation location 3 on the body, namely a device 100 for the controlled moving of the nozzle 10 and a device 102 with a controlledly movable holder 201 for the body 200; furthermore an electronic, programmable control device 102 for the devices 100 and 202. The nozzle 10 or the body 200 can also in each case be held in a spatially fixed position. The nozzle 10 (with the collimator tube 13) is connected via a flexible pressure line 14 to a partial plant which comprises or can comprise the following: a high pressure pump 101 for the production of the non-illustrated liquid jet and a device 103 for the treatment of the liquid, in particular for a filtering and/or a demineralization of the liquid. A reservoir for the liquid in a suitably treated form can also be provided (not illustrated).

What is claimed is:

1. Method for producing a surface structure, in particular on a surgical implant, through material ablation by means of a liquid jet (1) which is emitted from a nozzle (10) under high pressure (p), with an ablation location (3) being controlledly moved on a surface (20a) of a substrate (20) to be structured with the production of a predetermined macro-topography (2') or a largely planar surface, namely through moving the nozzle and/or the substrate, characterized in that the liquid of the high pressure jet (1) is emitted at a predetermined diameter d of the nozzle with a sufficiently high pressure p so that through the material ablation a linear track (2) with quasi-fractal micro-topography (4) is produced, with the track width D being at least twice as large as d and with values for p and d being provided in the following range:

100 bar<p<3000 bar and 0.1 mm<d<10 mm;

or p>3000 bar and d>0.03 mm.

2. Method in accordance with claim 1, characterized in that a medium which is largely free from solid particles is used as a liquid (1); and in that this liquid is in particular water, preferably suitably treated water.

3. Method in accordance with claim 1, characterized in that a group of ablation tracks (2) is produced which are locally largely parallel, with in each case a well recognizable ridge (22) or a practically non recognizable ridge being visible between adjacent tracks; or in that a non linear ablation track (8) is produced, the course of which is in particular meander-shaped.

4. Method in accordance with claim 3, characterized in that two or more groups (29, 29', 29") of tracks (2) are applied one over the other in a cross-wise arrangement.

5. Method in accordance with claim 1, characterized in that the distance (a) between an outlet opening (11) of the nozzle (10) and the surface (20a) to be processed amounts to about 0.1–20 mm; and in that the angle ($\beta$=90°–$\alpha$) between the liquid jet (1) and the ablation track (2) produced is 90° or preferably less than 90°.

6. Method in accordance with claim 1, characterized in that in a first or second step a further method for a surface processing, for example a sand blasting or a coating method is used, with the sand blasting method preferably being used in the first step.

7. Plant for carrying out the method in accordance with claim 1, comprising the following components: means (100, 202) for producing a relative velocity (v) between the body (200) to be processed and the ablation location, namely a controlledly movable holder (100) for the nozzle (10) and/or a controlledly movable holder (201) for the body, with it being possible to hold either the nozzle or the body in a spatially fixed position, furthermore, an electronic, programmable control device (102) for the means (100, 202) for producing the relative velocity and a high pressure pump (101) for a production of the liquid jet (1).

8. Plant in accordance with claim 7, characterized in that a device (103) for treating the liquid, in particular for a filtering and/or a demineralization of the liquid, is provided; or in that a reservoir for the liquid in suitably treated from is provided.

9. Use of the method in accordance with claim 1, characterized in that shaft surfaces of joint prostheses, which are preferably provided for a cementless implantation, or surfaces of dental implants are structured, with the surfaces to be structured being coated in a prior or subsequent treatment with a material which furthers the bone growth, in particular a calcium-phosphorus compound.

10. Use of the method in accordance with claim 1, characterized in that in an electro-physiological electrode one pole is structured at its surface in order—thanks to a large specific surface—to obtain an effective energy transfer from the pole to a tissue which is to be influenced physiologically, with the electrode in particular being part of a heart pacemaker or of a defibrillator.

11. Use of the method in accordance with claim 1, characterized in that materials are processed, namely for the production of structures at homogeneous, quasi-isotropic materials in order for example to achieve a corrugation or an orange skin effect, or the structuring of inhomogeneous materials, with different behavior being used relative to solubility or erosion.

* * * * *